United States Patent
Lee et al.

(10) Patent No.: US 8,134,025 B2
(45) Date of Patent: Mar. 13, 2012

(54) METHOD OF FABRICATING MESOCRYSTALS OF ORGANIC AND ORGANO-METALLIC COMPOUNDS

(75) Inventors: Tu Lee, Flushing, NY (US); Chyong-Wen Zhang, Chiayi (TW)

(73) Assignee: National Central University, Taoyuan County (TW)

( * ) Notice: Subject to any disclaimer, the term of this patent is extended or adjusted under 35 U.S.C. 154(b) by 0 days.

(21) Appl. No.: 12/076,253

(22) Filed: Mar. 14, 2008

(65) Prior Publication Data

US 2010/0228049 A1    Sep. 9, 2010

(30) Foreign Application Priority Data

Aug. 9, 2007    (TW) ............................... 96129464 A

(51) Int. Cl.
*C07C 53/134*    (2006.01)

(52) U.S. Cl. ....................................................... 562/496
(58) Field of Classification Search ....................... None
See application file for complete search history.

(56) References Cited

OTHER PUBLICATIONS

Colfen et al, Angew.Chem.Int.Ed. 2005, 44, 5576-5591.*

* cited by examiner

*Primary Examiner* — Sudhakar Katakam
(74) *Attorney, Agent, or Firm* — Jackson IPG PLLC; Demian K. Jackson

(57) ABSTRACT

The present invention fabricates mesocrystals of organic and organo-metallic compounds. Supersaturated solutions are made with different sums of an organic or organo-metallic compound and the organic or organo-metallic compound is added with an excipient. Through a water bath, mesocrystals are obtained from the supersaturated solutions with well-faceted nucleation and growth. Different polymorphisms are induced with different ratios of enantiomers. And the dissolution rate for fabricating the API is enhanced.

12 Claims, 1 Drawing Sheet

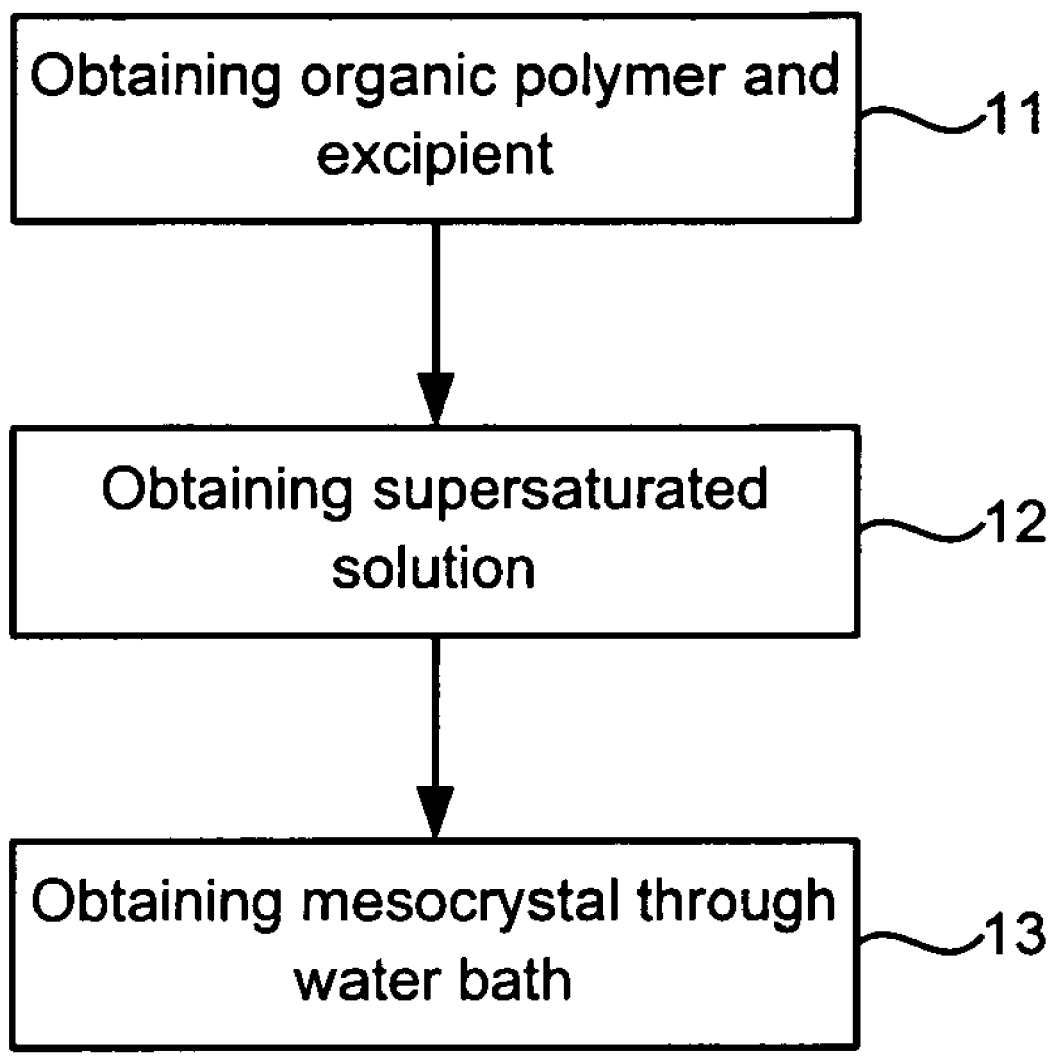

US 8,134,025 B2

METHOD OF FABRICATING MESOCRYSTALS OF ORGANIC AND ORGANO-METALLIC COMPOUNDS

FIELD OF THE INVENTION

The present invention relates to fabricating mesocrystals; more particularly, relates to obtaining different supersaturated solutions with an excipient for growing mesocrystals while inducing different polymorphisms with different ratios of enantiomers and enhancing the dissolution rate of the active pharmaceutical ingredients (APIs).

DESCRIPTION OF THE RELATED ARTS

Crystals of many chemical compounds are hard to be obtained. It is because the system is in lack of a stable seed. Even in a supersaturated environment, An enormous amount of external energy is still in need to obtain the seed by molecular collision for forming a new solid surface.

Mesocrystals are generally obtained by the key elements of minerals with polymers or surfactants as additives. However, mesocrystals with a well-faceted structure are hard to be induced.

In addition, traditional crystals are not constructed with nano-particles, so that they have relatively slow dissolution rates and thus are not good for fabricating APIs. Hence, the prior arts do not fulfill all users' requests on actual use.

SUMMARY OF THE INVENTION

The main purpose of the present invention is to obtain different supersaturated solutions with an excipient for growing mesocrystals while inducing different polymorphs and ratios of enantiomers, and enhancing the dissolution rate for fabricating APIs.

Another purpose of the present invention is to obtain mesocrystals having a well-faceted nucleation and growth.

To achieve the above purpose, the present invention is a method of fabricating mesocrystals of organic and organo-metallic compounds, comprising steps of: (a) obtaining an organic or organo-metallic compound and an excipient; (b) obtaining a supersaturated solution with the organic polymer and the excipient, placing the supersaturated solution in a glass vial and placing the glass vial in three constant temperature tanks; and (c) obtaining a mesocrystal through a water bath by: (c1) processing a stirring in the glass vial located in a first constant temperature tank; (c2) placing the glass vial in a second constant temperature tank, having a higher temperature than the first constant temperature tank, for stirring to completely dissolve the organic polymer; (c3) placing the glass vial back to the first constant temperature tank for staying still for a period of time; and (c4) rapidly moving the glass vial to a third constant temperature tank, having a lower temperature than the first constant temperature tank, for obtaining a mesocrystal in the glass vial. Accordingly, a novel method of fabricating mesocrystals of organic and organo-metallic compounds is obtained. (The glass vial can also stay in one tank and just let the temperature of the tank drop to a lower temperature.)

BRIEF DESCRIPTION OF THE DRAWING

The present invention will be better understood from the following detailed description of the preferred embodiment according to the present invention, taken in conjunction with the accompanying drawing, in which FIG. 1 is the flow view showing the preferred embodiment according to the present invention.

DESCRIPTION OF THE PREFERRED EMBODIMENT

The following description of the preferred embodiment is provided to understand the features and the structures of the present invention.

Please refer to FIG. 1, which is a flow diagram demonstrating a preferred embodiment according to the present invention. As shown in the FIGURE, the present invention is a method of fabricating mesocrystals of organic and organo-metallic compounds, comprising the following steps:

(a) Obtaining an organic or organo-metallic compound, and excipient 11: An organic and organo-metallic compounds, is obtained as a main element and an excipient is obtained as an additive.

(b) Obtaining a supersaturated solution 12: The organic or organo-metallic compound, is added with the excipient to obtain a supersaturated solution. Then the supersaturated solution is put in a glass vial having a cross-shaped magnetic spin bar inside. And the glass bottle is placed in a crystallizer. Therein, different supersaturated solutions are obtained with different sums of the organic or organo-metallic compound to meet different needs.

(c) Obtaining mesocrystal through water bath 13: A water bath is used with the crystallizer to obtain a mesocrystal, comprising the following steps:

(c1) Stirring in glass vial 131: A stirring is processed in the glass bottle located in a first constant temperature tank of the crystallizer.

(c2) Dissolving an organic or organo-metallic compound completely 132: The glass vial is then placed in a second constant temperature tank; and, a stirring is processed to completely dissolve the organic or organo-metallic compound, where the second constant temperature tank has a higher temperature than the first constant temperature tank.

(c3) Staying glass vial still 133: The glass vial is put back to the first constant temperature tank and is stayed still for a period of time.

(c4) Obtaining mesocrystal in glass vial 134: The glass vial is rapidly moved to a third constant temperature tank to obtain a mesocrystal in the glass vial, where the third constant temperature tank has a lower temperature than the first constant temperature tank.

With the above steps, a novel method of fabricating mesocrystals of organic and organo-metallic compounds is obtained, where different supersaturated solutions with an excipient are obtained for growing mesocrystals, different polymorphs are induced with different ratios of enantiomers, and the dissolution rate is enhanced for fabricating active pharmaceutical ingredients.

On using the present invention, the following steps' are taken:

(a) An organic compound (API) of racemic (R,S)-(±)-sodium ibuprofen dihydrate is obtained as a main element and an excipient of a deionized water is obtained as an additive.

(b) The organic compound has a weight of 6.7 to 6.8 grams (g); and the deionized water having a volume of 13 milliliters (ml) is added. Thus, a supersaturated solution is obtained under 25 Celsius degrees (° C.). The supersaturated solution is then put in a 20 ml glass vial having a cross-shaped magnetic spin bar; and the glass vial is put in a crystallizer having three constant temperature tanks. Therein, the racemic (R,S)-(±)-sodium ibuprofen dihydrate can have a weight of 6.7 g, 6.75 g or 6.8 g; the excipient can be sodium dodecyl sulfate having a density of 0.1 g per liter; and, so, different supersaturated solutions can be obtained with different sums of the organic or organo-metallic compound to meet different needs.

(c) A water bath is obtained with the crystallizer. Therein, the following steps are taken:
(c1) The glass vial is put in a first constant temperature tank of the crystallizer for stirring for 1 hour under 30° C.
(c2) The glass vial is then placed in a second constant temperature tank of the crystallizer for stirring for 30 minutes (min) under 40° C. to completely dissolve the organic or organo-metallic compound.
(c3) Then the glass vial is put back to the first constant temperature tank and is stayed still for 30 min.
(c4) Then the glass vial is rapidly moved to a third constant temperature tank of the crystallizer to obtain a mesocrystal under 25° C. in the glass vial.

In the third constant temperature tank, a conductivity meter is obtained to be inserted into the glass vial. Then a mouth of the third constant temperature tank is sealed for measuring a conductivity of the mesocrystal. During the measurement, after the excipient is added to racemic (R,S)-(±)-sodium ibuprofen dihydrate, a surface energetics is enhanced.

Thus, with the conductivity meter tracing relationships of concentration to time, spontaneous nucleation of mesocrystals with various supersaturated solutions are monitored to obtain a mechanism of the spontaneous nucleation. Furthermore, a differential scanning calorimetry (DSC) is used to analyze polymorphisms of the mesocrystals. With a scanning electron microscope (SEM), the mesocrystals are found to have curved edges, and there are deck-board and oriented-attachment structures among primary crystals. Through an analysis of powder X-ray diffraction (PXRD), the mesocrystals are found to have bottom-up single crystal structures. Thus, the crystals made according to the present invention have structures of nano-particles with perfect directional arrangements and are well-faceted mesocrystals.

To sum up, the present invention is a method of fabricating mesocrystals of organic and organo-metallic compounds, where different supersaturated solutions are obtained with an excipient for growing mesocrystals; different polymorphs are induced with different ratios of enantiomers; and the dissolution rate is enhanced for fabricating active pharmaceutical ingredients.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method of fabricating mesocrystals of racemic (R,S)-(±)-sodium ibuprofen dihydrate, comprising the steps of:
   (a) obtaining a mixture of racemic (R,S)-(±)-sodium ibuprofen dihydrate and a surfactant;
   (b) obtaining a supersaturated solution with said racemic (R,S)-(±)-sodium ibuprofen dihydrate and said surfactant, placing said supersaturated solution in a glass vial having a cross-shaped magnetic spin bar, and placing said glass vial in a crystallizer; and
   (c) obtaining a mesocrystal through a water bath with a crystallizer having three constant temperature tanks, comprising the steps of:
      (c1) processing a stirring in said glass bottle located in a first constant temperature tank of said crystallizer;
      (c2) placing said glass bottle in a second constant temperature tank of said crystallizer and processing a stirring to completely dissolve said organic or organo-metallic compound, wherein said second constant temperature tank has a higher temperature than said first constant temperature tank;
      (c3) placing said glass vial back to said first constant temperature tank and staying said glass vial still for a period of time;
      (c4) rapidly moving said glass vial to a third constant temperature tank of said crystallizer to obtain a mesocrystal in said glass bottle, wherein said third constant temperature tank has a lower temperature than said first constant temperature tank.

2. The method according to claim 1, wherein said surfactant is sodium dodecyl sulfate (SDS).

3. The method according to claim 1, wherein said racemic (R,S)-(±)-sodium ibuprofen dihydrate is obtained at a weight selected from a group consisting of 6.7 to 6.8 grams (g), 6.7 g, 6.75 g and 6.8 g.

4. The method according to claim 1, further comprising deionized water.

5. The method according to claim 2, wherein said sodium dodecyl sulfate has a concentration of 0.1 g per liter.

6. The method according to claim 4, wherein said deionized water has a volume of 13 milliliter.

7. The method according to claim 1, wherein a temperature of said first constant temperature tank is 30 Celsius degrees (° C.), a temperature of said second constant temperature tank is 40° C. and a temperature of said third constant temperature tank is 25° C.

8. The method according to claim 1, wherein said stirring in step (c1) is processed in said glass vial for 1 hour.

9. The method according to claim 1, wherein said stirring in step (c2) to completely dissolve said racemic (R,S)-(±)-sodium ibuprofen dihydrate is processed in said glass vial for 30 minutes (min).

10. The method according to claim 1, wherein said glass vial is held still for 30 min after being placed back to said first constant temperature tank in step (c3).

11. The method according to claim 1, wherein different supersaturated solutions are obtained with different sums of said organic or organo-metallic compound.

12. The method according to claim 11, wherein different polymorphs are obtained with said different supersaturated solutions.

* * * * *